US008686206B2

(12) United States Patent
Fang et al.

(10) Patent No.: US 8,686,206 B2
(45) Date of Patent: Apr. 1, 2014

(54) SINGLE LOOP MULTISTAGE FUEL PRODUCTION (75) Inventors: Howard L. Fang, Bridgewater, NJ (US); Moshe Ben-Reuven, Princeton, NJ (US); Richard E. Boyle, Philadelphia, PA (US); Robert M. Koros, Westfield, NJ (US)

(73) Assignee: Primus Green Energy Inc., Hillsborough, NJ (US)

( * ) Notice: Subject to any disclaimer, the term of this patent is extended or adjusted under 35 U.S.C. 154(b) by 405 days.

(21) Appl. No.: 12/942,680

(22) Filed: Nov. 9, 2010

(65) Prior Publication Data

US 2012/0116137 A1 May 10, 2012

(51) Int. Cl.
*C07C 1/04* (2006.01)

(52) U.S. Cl.
USPC .............. 585/317; 585/14; 585/318; 585/319

(58) Field of Classification Search
CPC ...................................... C07C 1/02; C07C 1/04
USPC .......................................................... 585/317
See application file for complete search history.

(56) References Cited

U.S. PATENT DOCUMENTS

| 3,894,102 A | | 7/1975 | Chang et al. | |
| 3,928,483 A | * | 12/1975 | Chang et al. | .................. 585/322 |
| 3,931,349 A | | 1/1976 | Kuo | |
| 4,011,275 A | | 3/1977 | Zahner | |
| 4,076,761 A | | 2/1978 | Chang et al. | |
| 4,304,951 A | | 12/1981 | Garwood et al. | |
| 4,347,397 A | | 8/1982 | Dwyer et al. | |
| 4,387,261 A | | 6/1983 | Chester et al. | |
| 4,481,305 A | | 11/1984 | Jorn et al. | |
| 4,482,772 A | | 11/1984 | Tabak | |
| 4,520,216 A | * | 5/1985 | Skov et al. | ..................... 585/315 |
| 4,973,784 A | * | 11/1990 | Han et al. | ....................... 585/475 |
| 5,321,183 A | * | 6/1994 | Chang et al. | .................. 585/475 |
| 6,444,712 B1 | * | 9/2002 | Janda | ............................. 518/706 |
| 2006/0231464 A1 | * | 10/2006 | Brignac et al. | ................ 208/142 |
| 2008/0228021 A1 | | 9/2008 | Joensen et al. | |
| 2009/0163751 A1 | | 6/2009 | Vora et al. | |
| 2010/0036186 A1 | | 2/2010 | Joensen et al. | |
| 2010/0240779 A1 | | 9/2010 | Nielsen et al. | |

OTHER PUBLICATIONS

Topp-Jorgensen, "Topsoe Integrated Gasoline Synthesis—the TIGAS Process," Methane Conversion, 1988, pp. 293-305, Elsevier Science Publishers, B.V., Amsterdam.

(Continued)

*Primary Examiner* — Walter D Griffin
*Assistant Examiner* — Jelitza Perez (57) ABSTRACT Synthetic fuels are produced from synthesis gas in a four-stage reactor system with a single recycle loop providing the requisite thermal capacity to moderate the high heat release of the reactions and to provide the reactants and reaction environments for the efficient operation of the process. The first stage converts a portion of the synthesis gas to methanol, the second stage converts the methanol to dimethylether, the third stage converts the methanol and dimethylether to fuel and the fourth stage converts the high melting point component, durene, and other low volatility aromatic components such as tri- and tetra-methylbenzenes to high octane branched paraffins.

23 Claims, 5 Drawing Sheets (56) References Cited

OTHER PUBLICATIONS

Simard et al., "ZnO-Cr2O3+ZSM-5 catalyst with very low Zn/Cr ratio for the transformation of synthesis gas to hydrocarbons," Applied Catalysis A: General 1995, pp. 81-98, vol. 125, Elsevier Science Publishers, B.V., Amsterdam.

Erena et al., "Conversion of syngas to liquid hydrocarbons over a two-component (Cr2O3) ZnO and ZSM-5 zeolite) catalyst: Kinetic modelling and catalyst deactivation". Chemical Engineering Science, 2000, pp. 1845-1855, vol. 55.

Yurchak et al., "Development of Mobil's Fixed-Red Methanol to Gasoline (MTG) Process". Methane Conversion, 1988, pp. 251-272, Elsevier Science Publishers, B.V. Amsterdam.

Allum et al., "Operation of the World's First Gas-to-Gasoline Plant". Methane Conversion, 1988, pp. 691-711, Elsevier Science Publishers, B.V., Amsterdam.

Yurchak et al., "Process Aging Studies in the Conversion of Methanol to Gasoline in a Fixed Bed Reactor", Independent Engineering Chemical Process Design and Development, 1979, pp. 527-534, vol. 18, No. 3.

* cited by examiner

SINGLE LOOP MULTISTAGE FUEL PRODUCTION

FIELD OF THE INVENTION

This invention relates to a new process to directly produce transportation fuels, such as gasoline, jet fuel and diesel from synthesis gas containing principally carbon monoxide, carbon dioxide, and hydrogen.

BACKGROUND OF THE INVENTION

The prior art describes several alternatives to produce gasoline and distillate from synthesis gas that do not anticipate the present invention of four reaction stages with an overall recycle loop to produce commercial quality fuels. Chang et al (U.S. Pat. No. 3,894,102) and Zahner et al (U.S. Pat. No. 4,011,275) propose that synthesis gas be passed over methanol producing catalyst with an acid component activity to convert methanol to dimethylether and then feeding this intermediate mixed product to a fuel producing stage with recycle of light components to mix with the intermediate mixed product feed.

In another example, Chang et al (U.S. Pat. No. 4,076,761) use synthesis gas produced from coal, shale and/or residua that is conveyed to a carbon oxide converter and thence to a fuel producing stage with recycle of light gases back to the synthesis gas stage, the carbon oxide conversion stage or the fuel producing stage.

Garwood et al (U.S. Pat. No. 4,304,951) disclose the advantage of hydrotreating only the heavy fraction of product from a fuel producing stage using ZSM-5 catalyst. The hydrotreating step is carried out using essentially pure hydrogen and isolated from the prior three stages to produce liquid fuel from synthesis gas.

Thereby, the referenced patents proceed with four sequential stages with separation of liquid intermediates and product concentration steps after the first, third and fourth stages, resulting in a complex and low efficiency process. In addition, due to the production of high melting point (~79° C.) durene, the cooling condenser ahead of the separator after the ZSM-5 stage needs a light gasoline recycle wash to keep it clean from durene deposition.

Haldor Topsoe (J. Topp-Jorgensen, "Topsoe Integrated Gasoline Synthesis—the TIGAS Process", in D. M. Bibby, C. D. Chang, R. W. Howe, S. Yurchak (Eds.), *Methane Conversion,* 1988, Elsevier Science Publishers, B. V., Amsterdam, 293-305) simplified the Mobil Methanol-to-gasoline (MTG) scheme by combining the first three stages within one synthesis gas recycle loop without intermediate separation utilizing a proprietary catalyst for the first step to enable it to operate effectively at the lower pressures required by the ZSM-5 step. Methanol production is equilibrium limited and conversion would be enhanced by operation at high pressure. However, at high pressures, ZSM-5 produces increasing amounts of the undesirable component, durene. The proprietary catalyst produced DME in addition to methanol to increase the conversion to oxygenates. At elevated pressure, however, ZSM-5 produces a gasoline with a very high heavy aromatic content, in particular with high concentrations of durene that then would require hydrotreating as in the MTG New Zealand plant. Operating at about 20 atmospheres, the durene level was more than about three times a satisfactory level and it was stated, though not shown, that an isomerization step could be introduced into the loop to bring the durene content close to equilibrium, which would give a satisfactory product (FIG. 9 of the article). The article does not show that it was demonstrated. The olefinic content of the product was reduced as the pressure of hydrogen was increased and was overall lower than in the Mobil MTG product thereby producing lowered Research and Motor Octanes.

In Skov et al (U.S. Pat. No. 4,520,216), three stages are sequenced with no intermediate separation using a single recycle loop with interstage heat exchange. This scheme produces an undesirable high durene content fuel. Jorn et al (U.S. Pat. No. 4,481,305) proposes a very complex set of recycles for a three-reaction stage configuration.

In still another configuration, catalytic activities of the first three stages were integrated into one catalyst for a one stage process (F. Simard, U. A. Sedran, J. Sepulveda, N. S. Figoli, H. I. de Lasa, Applied Catalysis A: General 125 (1995):81-98). The one-stage conversion process used a combined synthesis gas/methanol and methanol-to-gasoline catalyst, a $ZnO—Cr_2O_3+ZSM-5$ catalyst, that produced gasoline compounds from synthesis gas feed, however, the selectivity to carbon dioxide was extremely high, ca 70%, making the process impractical. The overall reaction is described by $2nCO+nH_2 \rightarrow (CH_2)_n+nCO_2$ with a minor amount of water (Javier Erena et al, Chemical Engineering Science 55 (2000) 1845-1855).

The complexity of the demonstrated and commercialized fixed bed Mobil Methanol-to-Gasoline (MTG) process can be appreciated from the description of the commercialized MTG process by Yurchak in D. M. Bibby, C. D. Chang, R. W. Howe, S. Yurchak (Eds.), *Methane Conversion,* 1988, Elsevier Science Publishers, B. V., Amsterdam, 251-272. In this process, synthesis gas is first converted to a methanol/water ($CH_3OH/H_2O$) mixture in a stand-alone plant. The methanol/water mixture is recovered and sent to intermediate tankage. Recycle is used to provide a heat sink for the highly exothermic reaction and to enhance synthesis gas conversion for this equilibrium limited reaction. The recycle gases are cooled to remove the methanol/water produced and must be reheated before returning to the reactor. The product methanol/water mixture from tankage is fed to a two stage reactor system containing a lead reactor with a catalyst that partially converts the methanol to dimethylether (DME) and then to another reactor with a recycle loop, the methanol-to-gasoline (MTG) reactor that converts the methanol/DME mixture to a heavy gasoline containing large amounts of durene, 1,2,4,5-tetramethyl benzene molecule that has a high freezing point (79.3° C.) and must be removed to make a viable gasoline product. The removal is effected by a hydrotreating step performed on a heavy fraction of the intermediate product from the fuel producing reactor stage and the hydrotreated fraction is combined with the light gasoline fraction to produce the gasoline product. The hydrotreater is operated at elevated pressure and is supplied with a hydrogen rich stream, which is produced from a portion of the synthesis gas by a separation step such as Pressure Swing Adsorption (PSA). The hydrotreating catalyst is presulfided and operated with a hydrogen rich gas recycle (Yurchak, 1985) and Garwood et al, (U.S. Pat. No. 4,304,951). One of the catalysts tested but rejected due to low activity is a presulfided commercial cobalt molybdate on alumina ($CoMoO_x/Al_2O_3$) catalyst.

The commercial plant built and operated in New Zealand using this scheme has the complexity of three recycle catalyst loops and three separation steps involving cooling the intermediate products to liquefy them to enable conventional separation and distillation steps and stepping down of pressures and recompression, one for making methanol one for making the raw gasoline and the third for removing the durene. Typical catalysts and conditions used in each step in the Mobil MTG plant built in New Zealand are shown in Table 5 below. It is clear from this abbreviated description that this prior art process is quite complex and inefficient in its handling of intermediate products and the recycles and it requires several high cost high pressure feed and recycle compressors, and high pressure pumps.

TABLE 5(a)

Prior Art MTG Reaction Sequence

| Principal Reactions | Feed | Catalysts | Typical Reactor Temperature, C. Note (1) | Typical Reactor Pressure, Atm Note (2) |
|---|---|---|---|---|
| $CO + H_2 \Leftrightarrow CH_3OH + H_2O$ | $CO, H_2$ | Reduced CuO/ZnO/$Al_2O_3$ | 230-290 | 50-100 |
| $CH_3OH \Leftrightarrow (CH_3)_2O + H_2O$ | $CH_3OH, H_2O$ | $\gamma$-$Al_2O_3$ | 310-320 | 18-22 pressure |
| $CH_3OH \Rightarrow (CH_2)_n + n\,H_2O$ | $CH_3OH, (CH_3)_2O, H_2O$ | ZSM-5 | 350-366 | 18-22 |
| $n/2(CH_3)_2O \Rightarrow (CH_2)_n + n/2H_2O$ | | | | |
| Durene $\Leftrightarrow$ iso-Durene | $(CH_2)_n, H_2$ | Sulfided Ni—W on $SiO_2/Al_2O_3$/faujasite | 220-270 | 30-40 |

Notes
(1) $(CH_2)_n$ with 4 < n < 10 denotes on the average the composition of the gasoline product which is a mixture of paraffins, iso-paraffins, olefins, cyclics and methyl substituted aromatics.
Note
(2) Reactor conditions from K.G. Allum and A.R. Williams, "Operation of the World's First Gas-to-Gasoline Plant", in D.M. Bibby, et al (Editors), Methane Conversion, 1988, Elsevier Science Publishers, B.V., Amsterdam, p691-711.

In the Mobil MTG process, durene is produced in enough quantities to result in undesirable cold temperature performance of the gasoline and must consequently be reduced. It is shown in Sergei et al. ("Process Aging Studies in the Conversion of Methanol to Gasoline in a Fixed Bed Reactor", Ind. Eng. Chem. Process Des. Dev., Vol. 18, No. 3, 1979) that ZSM-5 produces durene in much larger quantities than expected from equilibrium. This is shown in Table 5(b), which is an abstract of Table V of the reference.

TABLE 5(b)

| time on stream in cycle, h | | 11 | | 645 |
|---|---|---|---|---|
| maximum temperature, ° F. | 745 | 745 | 779 | 779 |
| tetramethylbenzenes, mol % | equil | exptl | equil | exptl |
| durene (1 ,2, 4, 5-) | 33.0 | 67.6 | 32.8 | 97.3 |
| isodurene (1, 2, 3, 5-) | 50.4 | 24.0 | 50.3 | 1.1 |
| prehnitine (1, 2, 3, 4-) | 16.6 | 8.4 | 16.9 | 1.6 |

Halving the amount of durene during an average cycle has been shown to produce a satisfactory fuel, therefore isomerizing the tetra-methyl-benzenes to an equilibrium mixture would be satisfactory to eliminate part of the problem. However, a certain amount of dealkylation of tetra-methyl-benzene is also provided by the catalyst used in the New Zealand plant (Garwood et al.).

Therefore, there remains a need for an efficient process to produce fuel from synthesis gas, whereby the fuel contains low amounts of durene and highly substituted benzenes for better viscometric properties in cold temperature performance.

SUMMARY OF THE INVENTION

This invention relates to a new process to directly produce transportation fuels, such as gasoline, jet fuel and diesel from synthesis gas containing principally carbon monoxide, carbon dioxide, and hydrogen. The synthesis gas may be produced from such raw materials as natural gas, coal, wood and other biological materials. The process entails four sequential catalytic stages with intermediate heat exchange to provide the requisite temperature in each stage, but with no interstage separation. The unreacted gases from the fourth stage are recycled to the first stage. The recycle enhances the conversion of the synthesis gas to the desired products and also serves as a heat sink for the highly exothermic reactions involved in each stage. This invention is distinct from the prior art in that it operates at elevated pressure, preferably about 50-100 atmospheres in all four stages, to yield high reactor utilization efficiencies to produces a hydrocarbon mixture ready for market as transportation fuels after the usual additives used in the industry are added. To the contrary, the prior art teaches that low pressures of 1 to 20 atmospheres in the third stage are required to produce acceptable transportation fuels.

This invention also provides a unique multistage process operating at essentially uniform pressure that converts synthesis gas to hydrocarbon fuels. Furthermore, the multistage process uses a single recycle loop connecting the last to the first stage. Cooling is preferably accomplished within and/or in-between stages to remove the exothermic heat of reaction produced in all stages.

The process contains four reactor stages in series, preferably interconnected with heat exchangers to adjust the temperature of the outflow of one stage to correspond to the desired inlet temperature of the next stage. Each stage may have one or more reactors in series or in parallel, loaded with the same catalyst. No separation or removal of intermediate product is made. The first stage converts synthesis gas to methanol and water; the second stage converts a portion of the methanol to dimethylether; the third stage converts methanol and dimethylether to gasoline and heavy gasoline; and the fourth stage converts the heavy gasoline via hydrotreating reactions to gasoline ($C_4$ to $C_8$), jet fuel, diesel or a combination thereof, as desired.

An additional uniqueness of this scheme is that the requisite hydrotreating reactions in the fourth stage are carried out in the presence of high concentrations of carbon monoxide, which are present in the recycle synthesis gas and is, in effect, used as the treat gas. We have discovered that there are a large variety of catalysts that may be used in the fourth stage to achieve the requisite reactions under these unique and unusual conditions of high partial pressure of carbon monoxide (carbon monoxide molar fraction in the fourth stage is about 20-25%). It is commonly taught in the art that the hydrotreating step should be carried out in the absence of substantial amounts of carbon monoxide to avoid poisoning of the catalyst.

The total flow exiting from the fourth stage is cooled to condense the product liquid hydrocarbon and water. These are removed from the recycle gases in a high pressure separator. The vapor from the high-pressure separator is split into two streams: a stream that is sent to fuel gas and LPG recovery and another larger stream that is sent to the recycle compressor for return to the feed of the first reaction stage. The recycle gas is composed of unreacted synthesis gas and small amounts of by-product light gases. The overall process yield is greater than about 25%, preferably about 15 to about 45% (based on weight of the converted synthesis gas). The fuel produced from the process preferably contains about 30 to about 40% straight and/or branched paraffins, more preferably C4 to C8, most preferably C5 to C7; about 15 to about 25% cyclic paraffins, preferably C6 to C8 hydrocarbons; about 2 to about 5% toluene; about 6 to about 10% xylenes; about 10 to about 15% trimethylbenzenes (TMB), and about 15 to about 20% durene and other tetra- or higher methyl-substituted benzenes.

The entire reactor system is operated at elevated pressure, 50 to 100 atmospheres, with modest pressure decreases due to pressure drop as a result of flow through the catalysts, pipes, and heat exchangers. This pressure drop is maintained at modest values to economize on the size and cost of the recycle compressor. The high pressure enhances the conversion of synthesis gas to the methanol intermediate in the first stage, has no effect in the conversion of methanol to the intermediate dimethylether. However, it is known in the art (Yurchak) that the conversion of ethanol/dimethylether to gasoline in the third stage also produces heavy gasoline, principally $\geq C_8$ aromatics, such as tri-methyl benzenes, tetramethyl benzenes, and durene. In particular, highly undesirable tetramethyl benzene and durene are produced which have high melting points (79° C. or greater) and limited solubility in the hydrocarbon mixture even at room temperature. Their viscometric behavior cannot be tolerated in an all-weather commercial fuel. In the present process, however, this intermediate product, containing heavy gasoline, is converted to desirable hydrocarbon products in the fourth stage by significantly reducing the trimethylbenzene and tetramethylbenzene and durene isomer groups via hydrotreating and producing desirable fuel compounds such as toluene, xylenes and $C_4$ to $C_8$ hydrobarbons, principally $C_5$ to $C_7$ hydrocarbons. This conversion is obtained by the proper choice of catalyst, space velocity and temperature of the reactor. The presence of heavy gasoline in the product produced from the third reaction is undesirable because it increases the freezing temperature of the fuel which renders the fuel unusable in cold weather. The fourth reactor converts the heavy gasoline to toluene, xylenes, and/or $C_4$ to $C_8$ hydrocarbon, which lowers the freezing point of the fuel product. Preferably, the fuel product coming out of the fourth reactor has a freezing point of less than about −5° C., preferably about −15 to about −20° C., while the product coming out of the third reactor has a freezing point of about 30-50° C.

The fourth stage catalysts that we have found to selectively accomplish this task are Group IX or X metal oxide (e.g. nickel oxide) catalyst on alumina reduced in the presence of hydrogen and carbon monoxide in the absence of sulfur. In certain embodiments, the catalyst can be Group IX or X metal oxide (e.g. cobalt oxide) catalyst combined with a Group VI metal oxide (molybdenum oxide) catalyst on alumina reduced in the presence of hydrogen and carbon monoxide and in the absence of sulfur. A specific example of the catalyst include unsulfided cobalt molybdate on alumina or atomic nickel on alumina, the reduction, if any, being carried out in the presence of synthesis gas. Sulfiding the catalyst surface is not necessary but catalytic reduction using either a $H_2$ flow or a mixture of $H_2$ and CO under operating temperature is desirable. Temperature of the fourth stage ranges from 120 to 230° C. (248 to 446° F.) depending on the catalyst used, with the preferred temperature being about 150-180° C. (302 to 356° F.). These temperatures are surprisingly lower than 232 to 427° C. (450 to 800° F.) disclosed by Garwood (U.S. Pat. No. 4,304,951) for treating a 200-400° F. bottoms fraction. We ascribe this valuable difference in temperature and the more desirable product mix to treating the whole product from the fuel forming step in the presence of synthesis gas instead of a bottoms fraction with principally hydrogen. We also ascribe this surprising result to using unsulfided catalysts, unlike Garwood that teaches by example that mixed oxide catalysts need to be sulfided. Han et al. (U.S. Pat. No. 4,973,784) teaches the use of zeolites for treating the durene containing product in the presence of substantial partial pressure of hydrogen producing undesirable benzene. Our novel process does not produce benzene. Still in another variation, Chester et al. (U.S. Pat. No. 4,387,261) propose treating the entire product from the fuel forming stage, but preferably a heavy fraction thereof, using ZSM-12, preferably impregnated with platinum, an expensive metal, at elevated temperatures and pressures to dealkylate durene to form xylene, toluene, benzene and undesirable light gases such as $C_2$ and $C_3$ hydrocarbon. The present process is clearly superior in that it does not produce light gases in the treating stage (stage 4). Still in another example, Dwyer et al. (U.S. Pat. No. 4,347,397), showed that treating the whole or bottoms product from the fuel producing stage with zeolites principally isomerizes the durene to other tetramethylbenzenes, thereby, producing less desirable heavy product than the present process.

Examples of catalysts and temperature ranges that can be used for the first three stages are as follows: in the first stage, R-1, $CuO/ZnO/Al_2O_3$ in the range of 190 to 300° C., with the preferred range of 220 to 260° C.; in the second stage, R-2, gamma-alumina in the range of 300 to 450° C. with the preferred range of 400 to 420° C.; and in the third stage, R-3, ZSM-5 in the range of 300 to 500° C. with preferred range of 343 to 420° C.

DETAILED DESCRIPTION OF THE PREFERRED EMBODIMENTS

Figure 1:
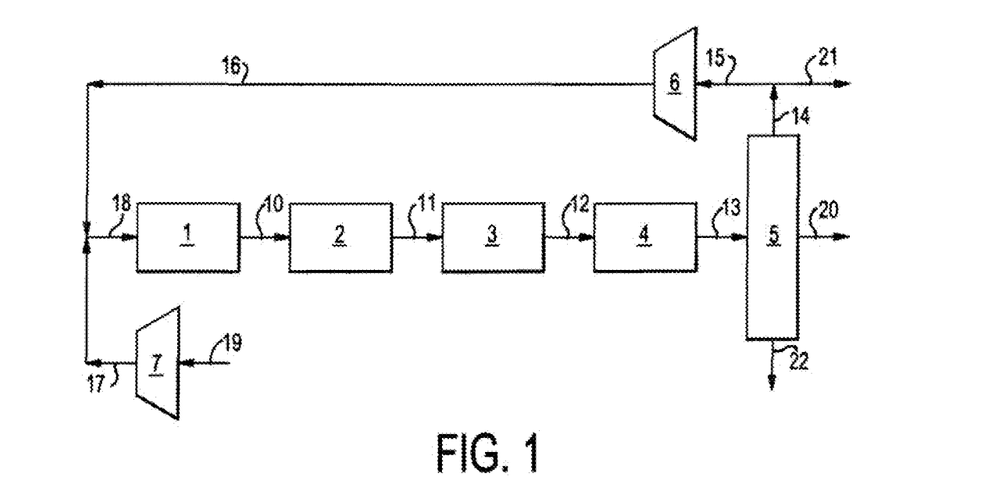
FIG. 1 is a schematic of a process of the present invention.

The invention will be readily understood from the Figures. Referring to FIG. 1, synthesis gas enters the process through conduit 19 at low pressure, and preferably is compressed by compressor 7 to 20 to 100 atmospheres, preferably 50 atmospheres, and is passed to the first reactor 1 via conduits 17 and 18. The first reactor 1 (R-1) converts synthesis gas to principally methanol and some water. The product from the first reactor 1, a vapor mixture of essentially methanol, water and unreacted synthesis gas, flows through conduit 10 to a second reactor 2 (R-2). The second reactor 2 converts a portion of the methanol to dimethylether. The product from second reactor 2, which essentially contains methanol, dimethylether, water and unreacted synthesis gas, flows via conduit 11 to a third reactor 3 (R-3). The third reactor 3 converts methanol and dimethylether to fuel product (gasoline, jet fuel and/or diesel) and heavy gasoline. The product from the third reactor 3 contains essentially fuel product (C4-C8 hydrocarbons, toluene, and xylene), heavy gasoline (≥C8 aromatics) and water, with minor amounts of unreacted methanol and dimethylether and unreacted synthesis gas. This product flows via conduit 12 to a fourth reactor 4 (R-4) to convert the heavy gasoline to fuel product. The product from the fourth reactor 4 contains essentially fuel product with low heavy gasoline content, water, minor amounts of unreacted methanol and dimethylether and unreacted synthesis gas, which pass via conduit 13 to a separator 5. The separator 5 separates the flow 13 into three streams: (a) conduit 22 carries out essentially water with some impurities for cleaning and reuse to make steam for the synthesis gas generating step not shown in the diagram; (b) conduit 20 carries out essentially fuel product that can be commercially marketed after addition of proper additives as required by commerce; and (c) conduit 14 carrying essentially light gases (including light paraffins below C4) and unreacted synthesis gas. The flow in conduit 14 is split into two streams: (a) flow through conduit 21 directed to further processing to recover LPG and excess gas for use as fuel for process heating needs; and (b) flow through conduit 15 is directed to a recycle compressor 6. The recycle compressor steps up the pressure of the recycle gas from losses through flow from conduit 18 to conduit 15 to match the inlet pressure of R-1 so that it can be mixed with the synthesis gas feed stream from conduit 17. The flow in conduits 15 and 16 is the greater part of the flow from conduit 14, being about 5 to 20 times larger than the flow in conduit 17, preferably 9 times larger.

Figure 2:
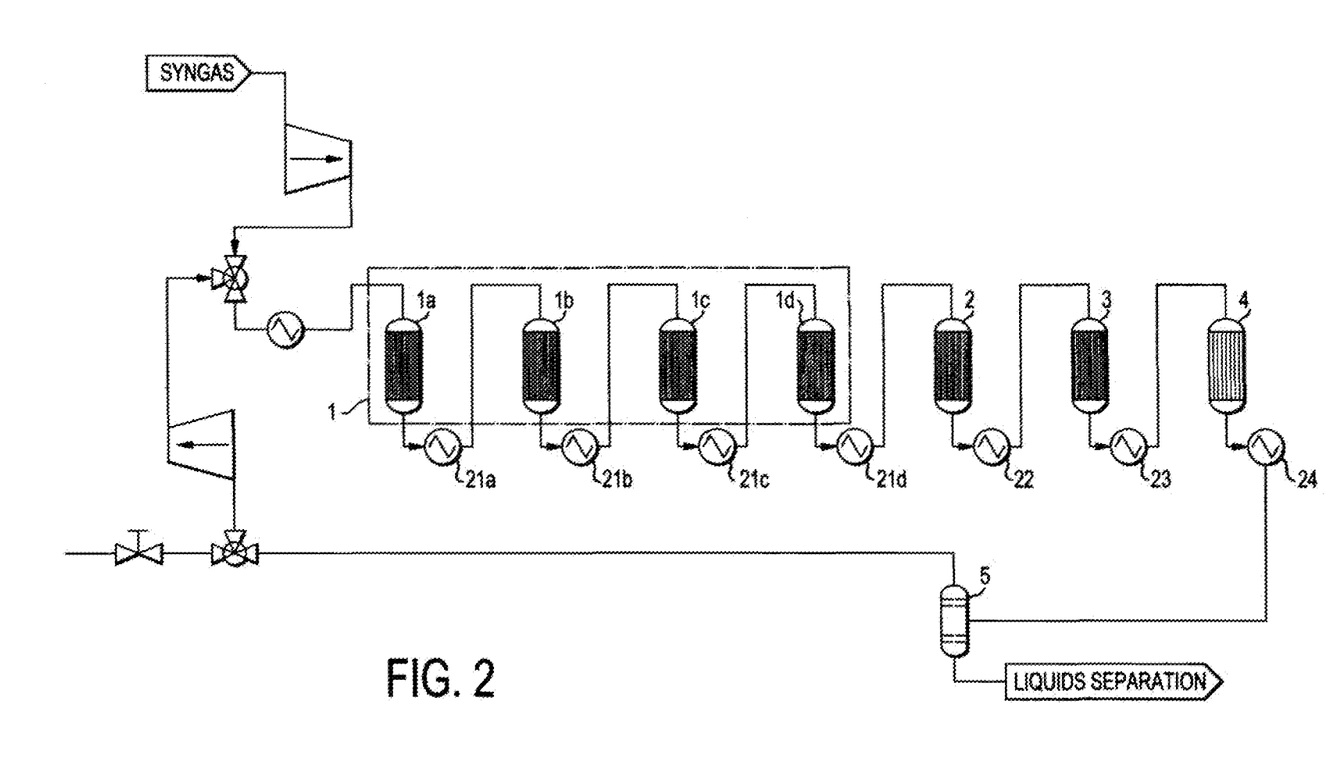
FIG. 2 is a schematic of an embodiment of the present process that includes four reactors in Stage 1.
Figure 3:
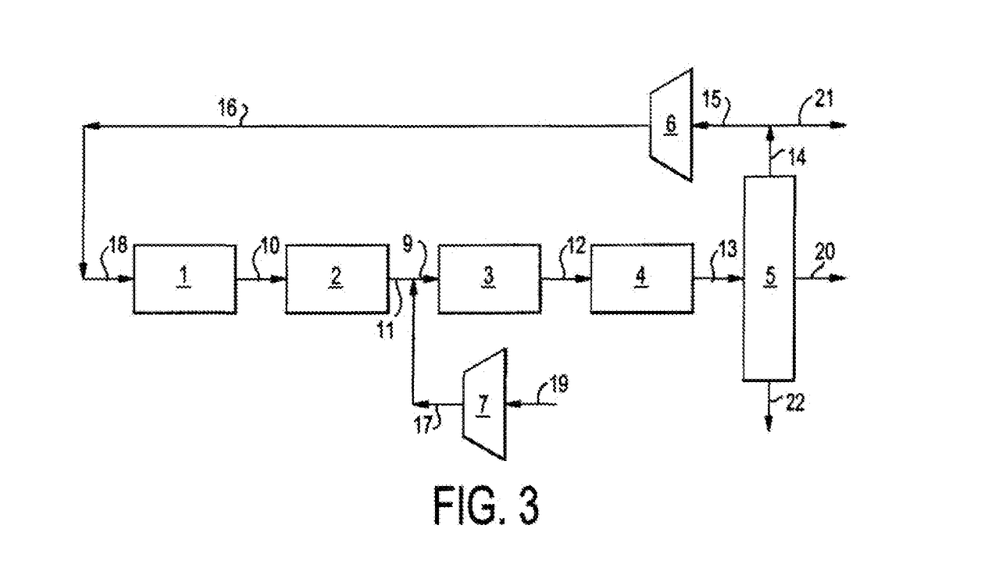
FIG. 3 is a schematic of an embodiment of the present invention that introduces the synthesis gas feed at the entrance of the third reactor (R-3).

Reactors 1 through 4 are preferably fixed bed reactors containing catalysts for effecting the desired reaction in each of the reactors. Due to the exothermicity of the reactions occurring in each stage, the reactors stages maybe sectioned with intermediate heat transfer to remove excess heat or the temperatures may be controlled via "cold-shot" side streams of cooled recycle gas for each stage or a combination of these two methods of temperature control may be used. FIGS. 2 and 3 show examples of these renditions, which are familiar to those skilled in the art. These examples do not limit the variations possible in the detailed design of this process.

FIG. 2 is a schematic of a further embodiment of the present process where the first reactor 1 contains four intercooled reactors (1a, 1b, 1c, and 1d) with heat exchangers (21a, 21b, 21c, and 21d) cooling the outlets of each of the reactors (1a, 1b, 1c, or 1d), respectively. Additionally, heat exchangers 22 and 23 are used to moderate the temperature of the exit flows of the second reactor 2 and the third reactor 3, respectively. An extra heat exchanger 24 is mounted between the fourth reactor 4 and the gas-liquid separator 5, to cool the outlet from the fourth reactor 4. The output from gas-liquid separator 5 is further divided into two parts: (1) the unreacted gas stream which will be fed into a control valve 40 to further separate into the recycled and the bleeding gas; and (2) the condensed liquid stream which can be fed into a fuel-water separator. Due to the difference in density between water and synfuel, the water accumulates at the bottom of the separator and can be drained out periodically.

FIG. 3 is a schematic of a further embodiment of the present process wherein the synthesis gas feed is introduced into the loop ahead of the third reactor 3 (R-3). Synthesis gas enters the process through conduit 19 at low pressure and is compressed by a compressor 7 to match the pressure of the flow passing out of the second reactor 2 (R-2) in conduit 11. The compressed synthesis gas in conduit 17 is mixed into the flow in conduit 11 to produce the flow in conduit 9 which is led into R-3. The flow in conduit 11 is the product from the second reactor 2 (R-2), which contains essentially methanol, dimethylether, water, and unreacted synthesis gas. R-3 converts the synthesis gas and olefins and other hydrocarbon contaminants in the synthesis gas feed passing in conduit 9 to a product which is essentially fuel product (principally C4-C8 hydrocarbons, toluene, and xylene), heavy gasoline (≥C8 aromatics) and water, with minor amounts of unreacted methanol and dimethylether and unreacted synthesis gas. The R-3 effluent passes through conduit 12 to the fourth reactor 4 (R-4) which converts the heavy gasoline to fuel product. The effluent from R-4, which is essentially fuel product with low durene content, water, minor amounts of unreacted methanol and dimethylether and unreacted synthesis gas, passes via conduit 13 to the separator 5. The separator 5 separates the flow 13 into three streams: (a) conduit 22 carries essentially water with some impurities for reuse, such as to make steam for the synthesis gas generating step not shown in the diagram; (b) conduit 20 carries essentially a fuel product which can be sold on the market after proper additives are added as required by commerce; and (c) conduit 14 carries essentially light gases and unreacted synthesis gas. The flow in conduit 14 is split into two streams with (a) flow through conduit 21 directed to further processing to recover LPG and excess gas for use as fuel for process heating needs; and (b) flow through conduit 15 directed to a recycle compressor 6. The recycle compressor steps up the pressure of the recycle gas from losses through flow from conduit 16 to conduit 15 to match the inlet pressure of R-3. The flow in conduits 15 and 16 is the greater part of the flow from conduit 14, being about 5 to 20 times larger than the flow in conduit 17, preferably 9 times or larger.

In FIG. 3, the feed synthesis gas is introduced and mixed into the recycle loop in the line between R2 and R3 instead of in the line to R1, as shown in FIG. 1. The principal advantage of this alternative over introducing the feed synthesis into R-1 is obtained in the case in which the synthesis gas contains alkane and/or olefin hydrocarbons molecules with two or more carbon atoms and/or larger cyclic and aromatic molecules. Although some olefin species may be in trace amounts, the catalysts residing in R-3 and R-4 convert the olefins directly into fuel product thus increasing the yield, prior to the reactions in R-1 and R-2. An additional advantage is that if this type of feed were to be fed into R-1, it would have to be first purified by a process, such as for example, extraction or steam reforming, to render the feed devoid of potential catalyst poisons for the R1 catalyst, such as olefins and aromatic molecules. In effect, in this rendition of the invention, third and fourth reactors 3 and 4 (R3 and R4) act as purifiers of the fresh feed synthesis gas for R-1, as it receives synthesis gas via the recycle loop.

Without further description, it is believed that one of ordinary skill in the art can, using the preceding description and the following illustrative examples, make and utilize the compounds of the present invention and practice the claimed methods. The following examples are given to illustrate the present invention. It should be understood that the invention is not to be limited to the specific conditions or details described in the examples.

Reactor Configuration and Methods Used for the Examples

The invention can be best described by giving examples from laboratory tests of the concept. A once-through pilot plant utilizing three "Berty-design" (Berty) internally recycled autoclave reactors were used in series for R-1 (the first reactor), R-2 (the second reactor), and R-3 (the third reactor) followed by an upflow 1.5"×12" long fixed bed reactor for R-4 (the fourth reactor). Each of these reactors simulates a reaction stage and it is clear to those familiar with the art that this process concept extends to the use of fixed bed reactors instead of one or more of the internally recycled reactors. The catalysts in the Berty reactors were loaded into a catalyst basket and the temperature of the bed was measured by a thermocouple inserted into the catalyst in each basket. The catalyst in R-4 was loaded in two layers separated by a metal screen support and alumina beads. The temperature was measured between the two beds. A by-pass system around R-4 permitted introducing or removing R-4 from the flow from R-3 to the product separator to demonstrate the beneficial effects of the fourth reaction stage. The tubing connections between reactors were heated with heating tape to prevent condensation of liquid intermediate and final products. The synthesis gas feed was supplied to R-1 as a mixture of CO, $H_2$ and an Ar tracer supplied in pressurized cylinders, metered using mass flow meters to give the desired composition. The pressure of the system was held constant by a backpressure regulator. The depressured gas was cooled by a water cooled condenser and a Jorgensen glass tube was used as a separator to separate the product liquid hydrocarbon, water and the synthesis gas containing light hydrocarbon gases not collected in the separator. The collected hydrocarbon liquid was analyzed by IR and GC-MS and the total hot gases after each reactor were sampled and analyzed using GC-MS. Material balance was achieved by using the Ar tracer and a massflow meter. The density of the collected liquid hydrocarbon was measured. The temperature inside each reactor was controlled via outer heater elements to temperatures set and measured in the inside of the catalyst beds.

A micro syringe with a fixed volume of 1 µl was used to inject the liquid fuel into the GC-MS system (HP7890). The reproducibility of the syringe is reasonably accurate and the volume fluctuation cannot exceed an uncertainty of more than 10%. Therefore, if a significant variation is observed for a specific species in the mass count from the GC-MS signal, the sampling fluctuation caused by the syringe sampling cannot account for such signal change. The signal variation must then come from compositional differences between the samples. Thus traces and quantitative mass counts or abundance of quadrupole detection can be used to compare process performance.

Being that the pilot plant was once-through and contained no recycle, the synthesis gas flow was set to represent the recycle case by restricting the conversion in R-1 to that calculated for a recycle case. Thus, for a once-through case of 10% conversion of synthesis gas to methanol in R-1, the once-through system would be simulating a 10:1 recycle rate for 100% conversion.

EXAMPLE 1

Figure 4:
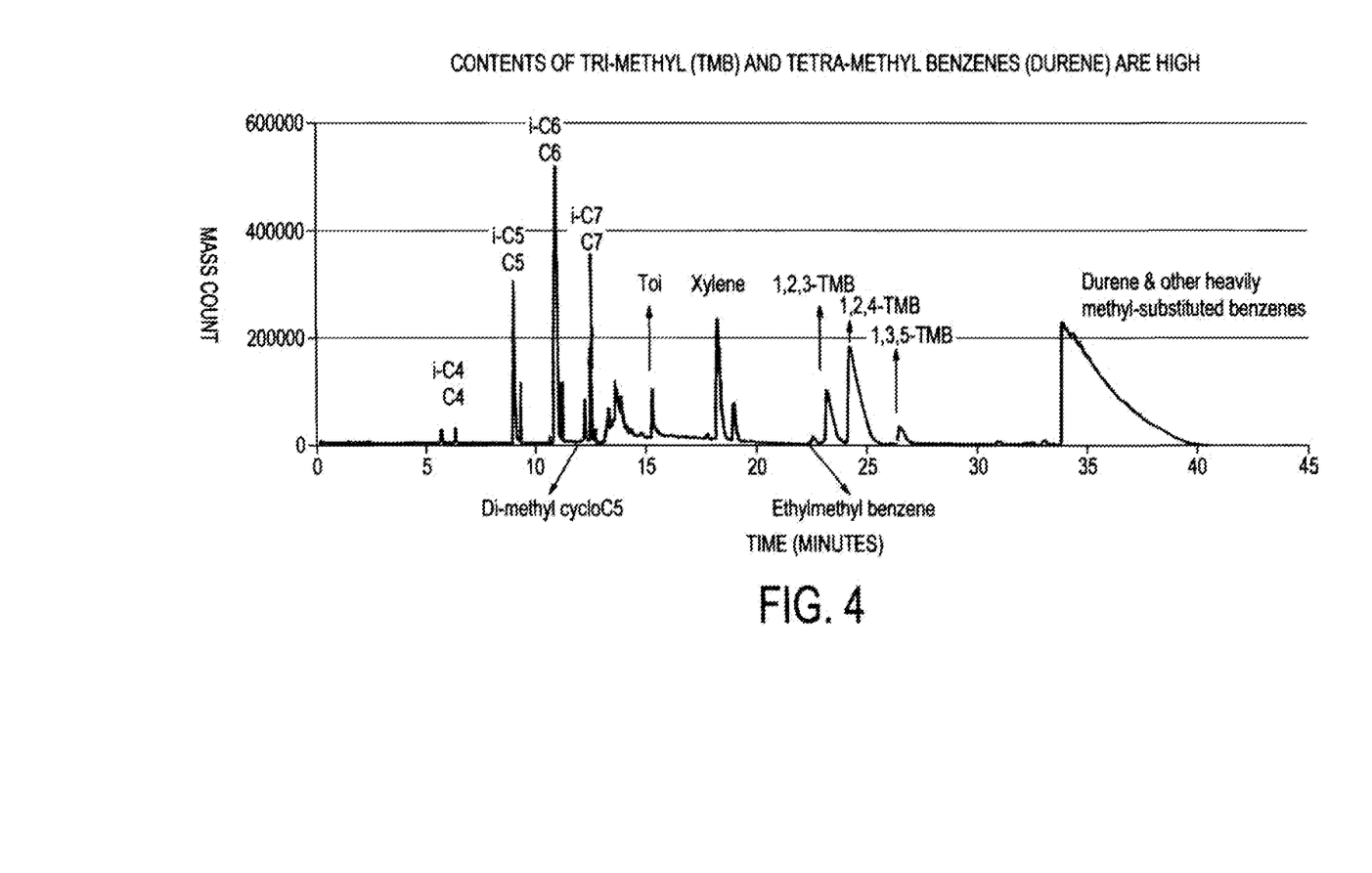
FIG. 4 is a GC-MS spectrum of a typical fuel obtained when the Reactor Stage 4 is not used.

In this example, R-1, R-2 and R-3 were used in-line with R-4 off-line to provide a base case for comparison to the beneficial effect of R-4 hydrotreating. R-1 contained 400 g of copper/zinc oxide/alumina (Katalco 51-9) catalyst, R-2 contained 200 g of gamma-alumina (SAS 250) and R-3 contained 200 g of the zeolite ZSM-5. The synthesis gas was composed of the following flows: 6130 scm$^3$ $H_2$. 2200 scm$^3$ CO, and 500 scm$^3$ Ar. Temperatures were as follows:

R-1, 280° C.; R-2, 385° C.; and R-3, 410° C. The pressure was 50 atmospheres at the outlet with minor pressure drop through the reactors. Liquid was collected in the separator at the rate of 6-7 g/h hydrocarbon together with by-product water. The hydrocarbon was analyzed by IR and GC-MS. The IR was used to confirm the identity of the components in the sample. The GC-MS results are shown in FIG. 4.

EXAMPLE 2

Figure 5:
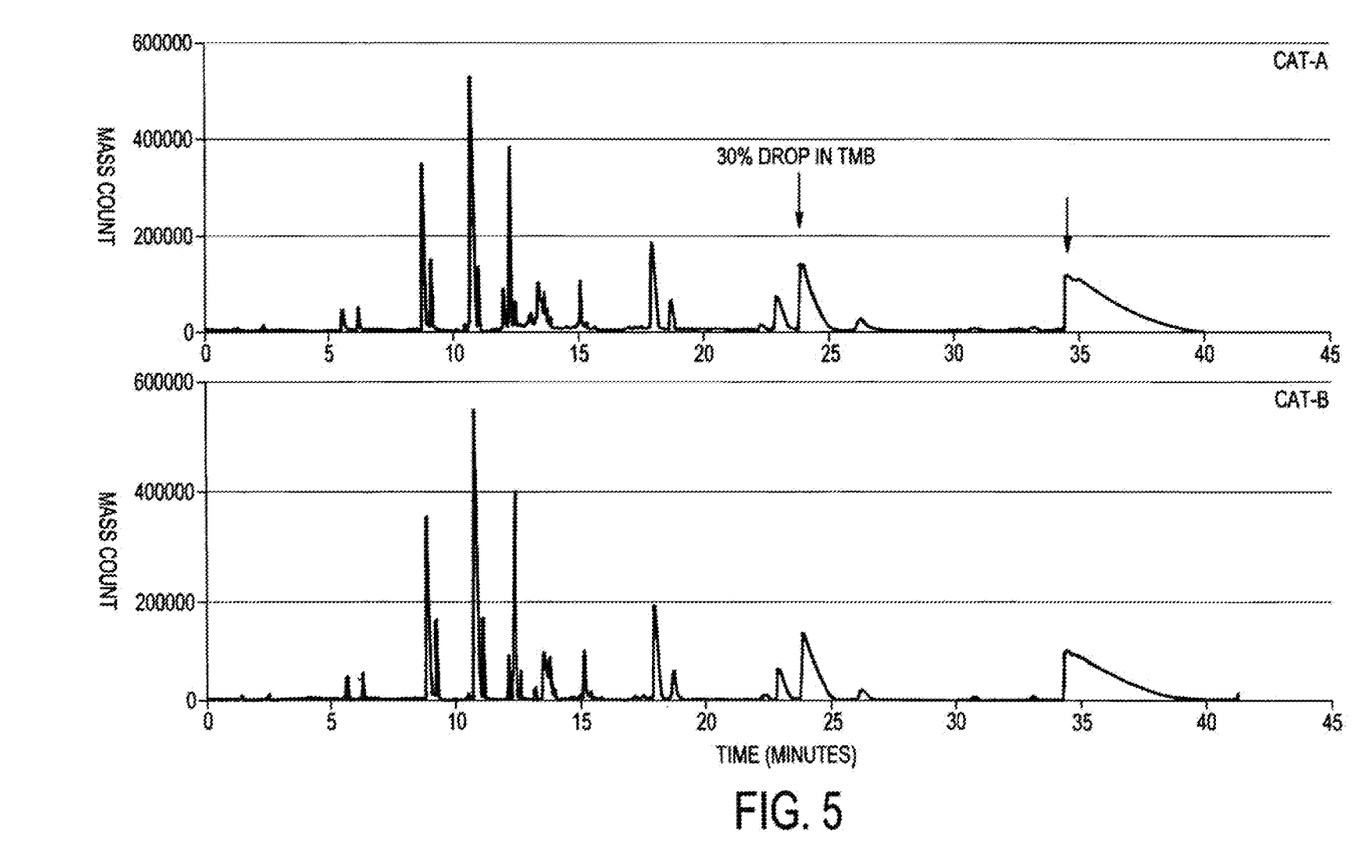
FIG. 5 is a GC-MS spectrum of the fuel product using the hydrotreating reactor (Reactor Stage 4) containing Catalyst A and Catalyst B.

In this example, R-1, R-2, R-3 line up, flows, temperatures and pressure were the same as in Example 1 and R-4 was added containing 50 g of catalyst-A (Criterion KL6515, a 60% Ni on alumina catalyst) held at 130° C. Liquid was collected in the separator at the rate of 7.04 g/h hydrocarbon and by-product water. The hydrocarbon was analyzed by IR and GC-MS. The GC-MS results in FIG. 5(*a*) show that the durene content was significantly reduced compared to Example 1, which did not utilize R-4.

EXAMPLE 3

In this example the reactor line-up and pressure were the same as in Example 2, however, the catalyst in R-4 was 50 g of catalyst-B (Alfa Aesar 45579, a cobalt molybdate on alumina) held at 140° C. Liquid was collected in the separator at the rate of 7.24 g/h hydrocarbon and by-product water. The hydrocarbon was analyzed by IR and GC-MS. The GC-MS results in FIG. 5(*b*) show that the durene content was significantly reduced compared to Example 1, which did not utilize R-4.

EXAMPLE 4

Figure 6:
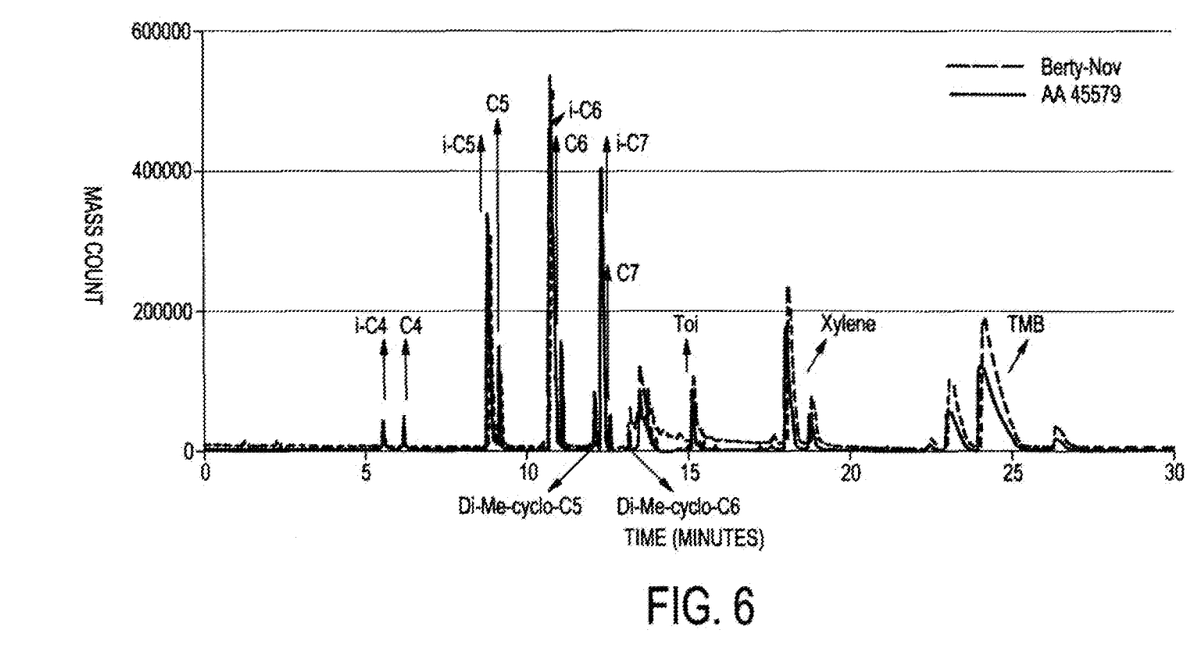
FIG. 6 is a comparison of fuel samples with and without Reactor Stage 4 with Catalyst A.

In this example, the GC-MS traces from Example 1 and Example 3 are superimposed for comparison and shown in FIG. 6 and quantified in Table 1. Table 1 lists the data of integrated area of all major bands for the liquid fuel samples with and without R-4. The catalyst used in R-4 is either cat-A (CRI-Critetrion KL6515) or cat-B (Alfa Aesar 45579). The retention times of individual band (in minutes) and the percentage changes derived from differences in band areas are also listed in Table 1 for comparison.

TABLE 1

| Species | Retention time (minutes) | Band area of the base fuel without R4 (×10$^5$) | Band area of the fuel using R4 with AA (×10$^5$) (% change from base) | Band area of the fuel using R4 with CRI (×10$^5$) (% change from base) |
|---------|--------------------------|------------------------------------------------|----------------------------------------------------------------------|------------------------------------------------------------------------|
| i-C4    | 5.64                     | 9.66                                           | 32.21 (+233%)                                                        | 26.40 (+173%)                                                          |
| C4      | 6.28                     | 7.04                                           | 23.91 (+239%)                                                        | 19.86 (+182%)                                                          |
| i-C5    | 8.91                     | 107.04                                         | 264.96 (+147%)                                                       | 201.05 (+87.8%)                                                        |
| C5      | 9.25                     | 21.88                                          | 60.77 (+178%)                                                        | 45.12 (+106.2%)                                                        |

TABLE 1-continued

| Species | Retention time (minutes) | Band area of the base fuel without R4 (×10⁵) | Band area of the fuel using R4 with AA (×10⁵) (% change from base) | Band area of the fuel using R4 with CRI (×10⁵) (% change from base) |
|---|---|---|---|---|
| i-C6 | 10.83 + 10.91 | 261.82 | 561.69 (+114%) | 408.61 (+56.1%) |
| C6 | 11.15 | 19.95 | 53.81 (+170%) | 39.54 (+98.2%) |
| Dimethyl-cyclo-C5 | 12.16 | 19.74 | 41.54 (+110%) | 21.67 (+9.8%) |
| i-C7 | 12.41 | 101.96 | 232.91 (+128%) | 165.83 (+62.6%) |
| C7 | 12.63 | 19.49 | 14.78 (−24%) | 13.12 (−32.7%) |
| Dimethyl-cyclo-C6 | 13.53 | 48.13 | 89.48 (+86%) | 70.52 (+46.5%) |
| Toluene | 15.22 | 60.68 | 48.62 (−19.8%) | 53.39 (−12%) |
| Xylene | 18.1 + 18.9 | 270.5 | 245.50 (−9.2%) | 256.63 (−5.1%) |
| TMB | 23.3 + 24.1 + 25.8 | 763.55 | 646.47 (−15.4%) | 660.11 (−13.5%) |
| Durene | 36-40 | 2238.70 | 1551.3 (−30.7%) | 1456.48 (−34.9%) |

It is interesting to note that all but the n-$C_7$ aliphatic portions, including $C_4$, $C_5$, $C_6$ and i-$C_7$, significantly increased for the fuels after R-4 hydrotreatment. All changes are significant, much more than 100% of the original values. Also, dimethylcyclopentane, dimethylcyclohexane, and other alkyl-substituted cyclic components increased. On the other hand, the areas under the curve for tri- and tetra-methylbenzene as well as toluene and xylenes are lower for the R-4 product, suggesting conversion from heavy aromatics to paraffins, naphthenes and less substituted aromatics.

We can simplify the data by grouping them with similar molecular size. For example, i-$C_4$ and $C_4$ can be grouped as $C_4$ total. The grouped data are listed in Table 2. As we group the data following molecular sizes, the increase using cat-A is 236% for $C_4$, 152% for $C_5$, 118% for $C_6$ and 103% for $C_7$; with larger increases for the smaller molecules, but on the basis of smaller amounts in the feed to R-4. The increase of cyclic components is relatively lower. For example, the increase for dimethylcyclohexane is 86% for cat-A and 46.5% for cat-B. All the substituted aromatics decreased across R-4 and most significantly because of their larger amount, trimethylbenzene and durene.

TABLE 2

| Species | Band area of the base fuel without R4 (×10⁵) | Band area of the fuel using R4 with AA (×10⁵) (% change from base) | Band area of the fuel using R4 with CRI (×10⁴) (% change from base) |
|---|---|---|---|
| $C4_{total}$ | 16.7 | 56.12 (+236%) | 46.26 (+177%) |
| $C5_{total}$ | 128.92 | 325.73 (+152%) | 246.17 (+90.9%) |
| $C6_{total}$ | 281.77 | 651.5 (+118%) | 448.15 (+59%) |
| Dimethyl-cyclo-C5 | 19.74 | 41.54 (+110%) | 21.67 (+9.8%) |
| $C7_{total}$ | 121.45 | 247.69 (+103%) | 178.95 (+47.3%) |
| Dimethyl-cyclo-C6 | 48.13 | 89.48 (+86%) | 70.52 (+46.5%) |
| Toluene | 60.68 | 48.62 (−19.5%) | 53.39 (−12%) |
| Xylene | 270.5 | 245.50 (−9.2%) | 256.63 (−5.1%) |
| TMB | 763.55 | 646.47 (−15.4%) | 660.11 (−13.5%) |
| Durene | 2238.70 | 1551.3 (−30.7%) | 1456.48 (−34.9%) |

The beneficial effect of the hydrotreatment is evident in that all desirable fuel components increased at the expense of significant decreases of the undesirable trimethylbenzenes and durene.

EXAMPLE 5

Further test were carried out at various R-4 temperatures and we found surprisingly that an optimum temperatures for R-4 exist to produce the highest rate of hydrocarbons. These results are shown in Table 3. It is clear that Catalyst-B exhibits a maximum fuel production rate at about 140° C., whereas Catalyst-A would appear to have an optimal temperature of about 130° C. The measurements suggest that the beneficial reactions that reduce the trimethyl- and tetramethybenzene including durene require a certain minimum temperature but as the temperature is further increased cracking reactions reduce the fuel yield.

TABLE 3

| Catalyst | R-4 Temperature, ° C. | Liquid Fuel Collected, g/h |
|---|---|---|
| Catalyst-A | 130 | 7.04 |
|  | 170 | 6.11 |
|  | 190 | 5.39 |
|  | 220 | 5.15 |
| Catalyst-B | 120 | 6.03 |
|  | 140 | 7.24 |
|  | 160 | 5.83 |
|  | 180 | 4.83 |

EXAMPLE 6

The product from R-4 has significantly improved in viscometric properties over that obtained from R-3. The freezing point of the fuel was decreased and the viscosity was decreased. The fuel color is also changed from yellow to colorless. However the density of the fuel was not significantly changed indicating that the aromatic content was not changed significantly. The fuel density at room temperature from R-3 was 0.83 g/ml and from R-4, 0.82 g/ml.

EXAMPLE 7

This example compares the fuel product rate with and without R-4 as given in Examples 1, without R-4 and Example 5 with R-4. Table 4 below shows the comparison:

TABLE 4

|  | R-4 Temperature, °C. | Fuel Rate, g/h |
|---|---|---|
| Without R-4 |  | 5-6 |
| With R-4 Catalyst-A | 130 | 7.0 |
| With R-4 Catalyst-B | 140 | 7.2 |

The comparison shows that, by producing a more advantageous mix of hydrocarbons, R-4 enhanced the recovery of fuel.

Although certain presently preferred embodiments of the invention have been specifically described herein, it will be apparent to those skilled in the art to which the invention pertains that variations and modifications of the various embodiments shown and described herein may be made without departing from the spirit and scope of the invention. Accordingly, it is intended that the invention be limited only to the extent required by the appended claims and the applicable rules of law.

What is claimed is:

1. A process for making fuel from synthesis gas comprising the steps of
    a) passing the synthesis gas through a first reactor to convert synthesis gas to methanol and water, which produces a first exit stream;
    b) passing the first exit stream through a second reactor to convert methanol to dimethylether, which produces a second exit stream;
    c) passing the second exit stream through a third reactor to convert methanol and dimethylether to fuel and heavy gasoline, which produces a third exit stream;
    d) passing the third exit stream through a fourth reactor to convert the heavy gasoline to isoparaffins and naphthenes which produces a fourth exit stream; and
    e) recycling the unreacted synthesis gas in the fourth exit stream to the first reactor;
    wherein no removal or separation of the first, second or third exit streams are effected during the process.

2. The process of claim 1, wherein the first, second, third, and fourth reactors operate at about 50-100 atmospheres.

3. The process of claim 1, wherein the fuel contains essentially C4-C8 hydrocarbons, toluene and xylene.

4. The process of claim 1, wherein the heavy gasoline contains ≥C8 aromatics.

5. The process of claim 1, the first reactor operates at about 190 to 300° C.

6. The process of claim 1, wherein the second reactor operates at about 300 to 450° C.

7. The process of claim 1, wherein the third reactor operates at about 300 to 500° C.

8. The process of claim 1, wherein the fourth reactor operates at about 100 to 220° C.

9. The process of claim 1, wherein the first reactor contains $CuO/ZnO/Al_2O_3$ catalysts.

10. The process of claim 1, wherein the second reactor contains gamma-alumina catalysts.

11. The process of claim 1, wherein the third reactor contains ZSM-5 catalysts.

12. The process of claim 1, wherein the fourth reactor contains Group IX or X metal oxide catalyst on alumina reduced in the presence of hydrogen and carbon monoxide and in the absence of sulfur.

13. The process of claim 12, wherein the Group IX or X metal oxide is nickel oxide.

14. The process of claim 1, wherein the fourth reactor contains Group IX or X metal oxide catalyst combined with a Group VI metal oxide catalyst on alumina reduced in the presence of hydrogen and carbon monoxide and in the absence of sulfur.

15. The process of claim 14, wherein the Group IX or X metal oxide is cobalt oxide and the Group VI metal is molybdenum oxide forming cobalt molybdate.

16. The process of claim 1, wherein prior to step e), the fourth exit stream is separated into a first stream containing water, a second stream containing unreacted synthesis gas, and a third stream containing fuel.

17. The process of claim 1, wherein the first, second, and third exit streams are heated or cooled prior to being passed through the second, third, and fourth reactors, respectively.

18. The process of claim 1, wherein the heavy gasoline contains trimethyl benzene, tetramethyl benzene, and durene.

19. The process of claim 1, wherein the third exit stream has a freezing point of about 30 to about 50° C.

20. The process of claim 1, wherein the fuel has a freezing point of less than about −5° C.

21. The process of claim 1, wherein the yield of the fuel is greater than about 25% by weight based on the synthesis gas.

22. The process of claim 1, wherein the synthesis gas is initially passed directly into the third reactor.

23. The process of claim 22, wherein the synthesis gas contains alkane and/or olefin hydrocarbons molecules with two or more carbon atoms and/or larger cyclic and aromatic molecules.

* * * * *